United States Patent
Wang

(10) Patent No.: US 11,091,731 B2
(45) Date of Patent: Aug. 17, 2021

(54) METHOD FOR FACILITATING AEROBIC FERMENTATION REACTION USING COMBUSTION WASTE GAS

(71) Applicant: Hunan Sakal Environmental Science and Technology Co., Ltd., Changsha (CN)

(72) Inventor: Shen Wang, Changsha (CN)

( * ) Notice: Subject to any disclaimer, the term of this patent is extended or adjusted under 35 U.S.C. 154(b) by 1091 days.

(21) Appl. No.: 15/494,520

(22) Filed: Apr. 23, 2017

(65) Prior Publication Data

US 2017/0226464 A1    Aug. 10, 2017

Related U.S. Application Data

(63) Continuation of application No. PCT/CN2014/090220, filed on Nov. 4, 2014.

(30) Foreign Application Priority Data

Oct. 23, 2014   (CN) .......................... 201410567892.3

(51) Int. Cl.
  *C12M 1/34* (2006.01)
  *C12M 1/02* (2006.01)
  *C12M 1/00* (2006.01)
  *C12Q 3/00* (2006.01)

(52) U.S. Cl.
  CPC ............ *C12M 41/34* (2013.01); *C12M 29/06* (2013.01); *C12M 41/12* (2013.01); *C12M 41/20* (2013.01); *C12M 43/04* (2013.01); *C12Q 3/00* (2013.01)

(58) Field of Classification Search
  CPC .................................................. C12M 43/04
  See application file for complete search history.

(56) References Cited

FOREIGN PATENT DOCUMENTS

WO    WO-2011139163 A1 * 11/2011 ............... C12N 1/20

OTHER PUBLICATIONS

Liew et al. Liquid, Gaseous and Solid Biofuels: conversion techniques, 2013, Chapter 5, pp. 125-173.*
Gunnarsson et al. Environmental Science and Teachnology, Oct. 2, 2014, pp. 12464-12468.*

* cited by examiner

*Primary Examiner* — Bin Shen
(74) *Attorney, Agent, or Firm* — Erson IP (Nelson IP)

(57) ABSTRACT

Provided is a method for facilitating an aerobic fermentation reaction using combustion waste gas, wherein organic waste in a reactor is heated using waste gas with heat produced from fuel combustion to facilitate the fermentation reaction, some of the chemical substances in the waste gas with heat produced from fuel combustion are absorbed by the organic waste in the reactor, and an environmental friendly treatment is performed on the waste gas with heat produced from fuel combustion. The specific practices comprise: connecting a gas outlet of a combustion device to a conveying pipe, and then connecting the conveying pipe to a gas inlet of the reactor or an air chamber aeration nozzle at a lower part of the reactor. Not only the equipment and cost for combustion waste gas treatments are saved, but also the aerobic fermentation efficiency of the organic waste is improved, which reduces the fermentation time. Not only the combustion waste gas is treated for environmental protection, but also the environmental friendly treatments of organic refuse waste are facilitated; and thus the method is an energy saving and environmental friendly technique.

4 Claims, 1 Drawing Sheet

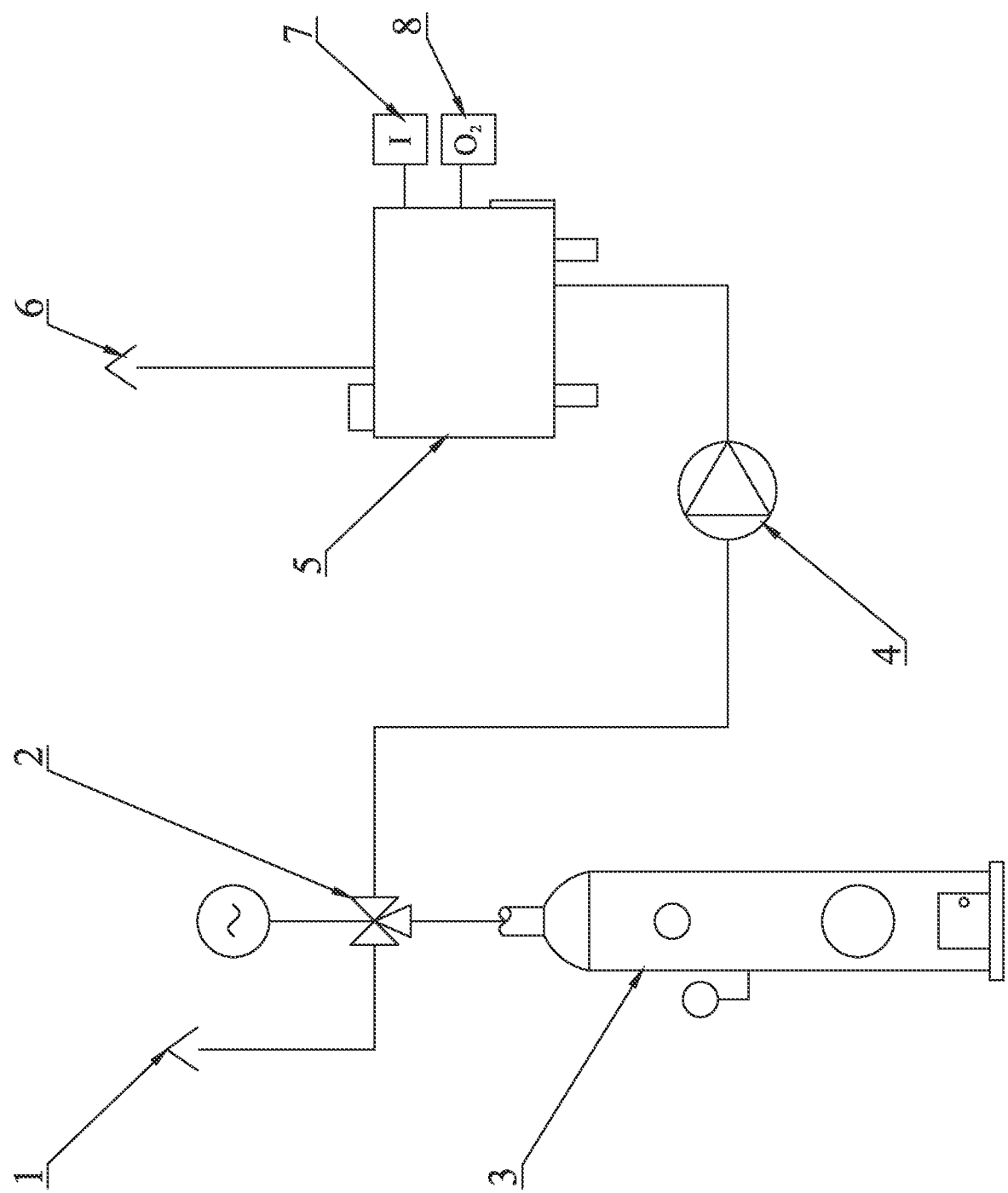

METHOD FOR FACILITATING AEROBIC FERMENTATION REACTION USING COMBUSTION WASTE GAS

CROSS-REFERENCE TO RELATED APPLICATIONS

This application is a continuation of International Patent Application No. PCT/CN2014/090220 with an international filing date of Nov. 4, 2014, designating the United States, and further claims priority benefits to Chinese Patent Application No. 201410567892.3 filed Oct. 23, 2014. The contents of all of the aforementioned applications, including any intervening amendments thereto, are incorporated herein by reference.

FIELD OF THE INVENTION

The present application relates to the fields of bio-fermentation and combustion waste gas treatment, and more particularly relates to a method for facilitating an aerobic fermentation reaction using combustion waste gas.

BACKGROUND OF THE INVENTION

A large amount of organic wastes are produced in livestock and poultry breeding farms and during industrial production and domestic living, which will lead to severe pollution without effective treatment. Thus, various methods, such as composting, methane fermentation, landfilling, and incineration and so on, are adopted to treat the organic wastes.

At the present, large fermentation reactor for aerobic or anaerobic fermentation is mainly heated by way of direct heating or indirect heating. For example, the direct heating refers to blowing hot air into the reactor to heat the materials; and the indirect heating refers to indirectly heating the materials through heating inner wall or coiled inner pipe of the reactor. However, both the direct and indirect heating methods have some problems, for example the energy consumption for blowing hot air into the reactor to heat the materials is very high, and the energy is seriously wasted; and the indirect heating method has the problem of low warming speed and high energy consumption. For example Chinese patent No. 201210060507.7 discloses a system and method for aerobic fermentation reaction with high efficiency and intelligence. In the patent, the organic materials are heated indirectly via circulating water in the interlayer. This method has the problems of low warming speed, high energy consumption, complex circulating water system and high cost and so on.

Fuels, such as coal, natural gas and diesel oil and so on, will produce large amount of heat during the combustion. Some of the heat is discharged together with the waste gases which comprise a large amount of heat, particulate matter such as smoke dust, carbon monoxide (CO), toxic gases such as sulfur dioxide ($SO_2$) and nitrogen oxides ($NO_x$). If the waste gases are directly discharged, the air will be polluted seriously, such as causing the environmental problems of acid rain, green-house effect, and haze, and hence seriously affecting physical health and production and life. At the present, in the treatments of the waste gases produced in combustion of the fuels such as coal, natural gas and diesel oil, the treatment to heat is mainly in way of absorbing the heat by a cooling device. The cooled gases are then absorbed and converted by physical, chemical and biological methods and discharged after achieving discharge standards. Most of the heat in the waste gases is unutilized or the utilization rate is very low. Even though the heat in the waste gases is utilized, the cost is also very high. Chinese patent No. 200910216681 discloses a system for treating combustion waste gases of fossil fuels by biological method. In this system, the heat in the waste gases is absorbed by a cooling tower, and then atomized via ultrasonic wave. However, this part of heat is only treated, but unutilized. Moreover, adopting the cooling tower to absorb heat will increase the cost.

SUMMARY OF THE INVENTION

Aiming at the problems of heating in biological fermentation of organic waste and of treatment of the fuel combustion waste gas in the prior art, the objective of the present application is to provide a method for facilitating an aerobic fermentation reaction using combustion waste gas. This method skillfully combines the biological fermentation and treatment of the fuel combustion waste gas together, not only saves the equipment and cost for combustion waste gas treatments, but also improves the aerobic fermentation efficiency of the organic waste, which reduces the fermentation time. Here was both energy conservation and environmental protection upon a single cast.

The technical solutions of the present invention are as follows:

A method for facilitating an aerobic fermentation reaction using combustion waste gas is provided, wherein organic waste in a reactor is heated using waste gas with heat produced from fuel combustion to facilitate the fermentation reaction; some of the chemical substances in the waste gas with heat produced from fuel combustion are absorbed by the organic waste in the reactor; and an environmental friendly treatment is performed on the waste gas with heat produced from fuel combustion.

Advantageously, the organic waste in the reactor is heated using the waste gas with heat produced from fuel combustion by a specific way of: connecting a gas outlet of a combustion device to a conveying pipe, and further connecting the conveying pipe to a gas inlet of the reactor or an air chamber aeration nozzle at a lower part of the reactor.

Advantageously, a wind turbine is connected in series between conveying pipes.

Advantageously, the fuel comprises coal, natural gas diesel oil, heavy oil, or biomass.

Advantageously, the organic waste in the reactor is heated using the waste gas with heat produced from fuel combustion by a specific way of: mixing the waste gas with heat with external air according to a preset ratio, and ventilating the mixture into the reactor of aerobic fermentation to heat the organic waste in the reactor of aerobic fermentation.

Advantageously, the chemical substances in the waste gas with heat absorbed by the organic waste in the reactor comprise $SO_2$, $NO_2$, $CO_2$, and dioxin.

Advantageously, the tee valve and the ratio adjusting device are capable of mixing the waste gas and the external air according to the preset ratio.

Advantageously, the organic waste in the reactor is heated using the waste gas with heat produced from fuel combustion under the control of a controller; an oxygen sensor and a temperature sensor are mounted at a discharge end of the reactor, outputs of the oxygen sensor and the temperature sensor are connected to corresponding inputs of the controller respectively, and the controller is capable of comparing input values from the sensors with present values so as to control a tee valve and a ratio adjusting device for mixing the waste gas with heat with external air according to a preset ratio; when the controller detects that oxygen content from the oxygen sensor is lower than a present lower limit value, the controller controls the tee valve and the ratio adjusting device to increase the ratio of the external air, and when the controller detects that the oxygen content from the oxygen sensor is higher than a preset upper limit value, the controller controls the tee valve and the ratio adjusting device to decrease or zero the ratio of the external air; when the controller detects that temperature from the temperature sensor is higher than a present value, the controller controls the tee valve and the ratio adjusting device to decrease or zero the ratio of the waste gas; and when the controller detects that the temperature from the temperature sensor is lower than a present value, the controller controls the tee valve and the ratio adjusting device to increase the ratio of the waste gas.

Advantageously, the waste gas with heat is mixed with the external air according to the preset ratio before being ventilated into the reactor of aerobic fermentation, and the preset ratio is 0~1:1~0.

Advantageous Effects:

The present invention combines the biological fermentation and treatment of combustion waste gas together in which the fermentation reactor is heated by the heat contained in the combustion waste gas so as to facilitate fermentation reaction and keep the fermentation continuously with a high efficiency. The gases generated by burning the fuels, such as coal, natural gas, biomass and diesel oil and so on, contain a large amount of fine particles such as PM2.5. These particles can be absorbed by organic materials, and some of them are converted into useful nutrients. Meanwhile, some gases in the waster gas, such as sulfur dioxide and nitrogen dioxide and so on, can combine with the water in the organic materials in the fermentation reactor, and release $H^+$, which is helpful to decrease the pH of the organic materials and neutralize the organic materials, so that the release of ammonia and nitrogen in the organic materials can be reduced and the loss of nutritive elements can also be reduced. Last but not least, the gases discharged from the fermentation reactor are treated by the biological filtration tower, which avoids the generation of secondary pollution. In conclusion, the present method is energy saving and environment friendly, improves fermentation efficiency, reduces fermentation time and reduces producing cost.

The present invention solves the problems of cooling, dust removal and purification treatments of the high-temperature flue-gases generated from the combustion devices in the prior art such as boiler, kiln, diesel generator, thermal power plant, combustor and so on. However, it needs a large amount of devices, capital and energy to solve these environmental treatment problems according to the prior art. Meanwhile, the present invention further solves the problem of heating of the organic waste materials in the aerobic fermentation reaction, which also needs a large amount of devices, capital and energy according to the prior art. The present invention skillfully combines the two together and turns "waste" into wealth. In one aspect, for the combustion waste gas, its heat is used to heat the organic wastes in the fermentation reaction, which replaces the cooling equipment of the combustion device. In another aspect, the harmful gases and dusts in the combustion waste gas are absorbed by the organic wastes in the fermentation reaction, which functions as purification. In this way, for the aerobic fermentation reaction of the organic wastes, the energy is significantly saved, and the equipment and costs are largely reduced. Accordingly, the present invention skillfully combines the two together and is an energy saving and environment friendly technique with extremely obvious effects.

BRIEF DESCRIPTION OF THE DRAWINGS

FIG. 1 is structural diagram of the present invention.
Wherein in the drawings:
1-chimney, 2-electric tee valve, 3-combustion device, 4-wind turbine, 5-fermentation reactor, 6-exhaust outlet, 7-temperature sensor, 08-oxygen sensor.

DETAILED DESCRIPTION OF THE PREFERRED EMBODIMENT

Referring to FIG. 1, in the method for facilitating an aerobic fermentation reaction using combustion waste gas according to the present invention, organic waste in a reactor is heated using waste gas with heat produced from fuel combustion to facilitate the fermentation reaction; some of the chemical substances in the waste gas with heat produced from fuel combustion are absorbed by the organic waste in the reactor, and an environmental friendly treatment is performed on the waste gas with heat produced from fuel combustion.

The organic waste in the reactor is heated using the waste gas with heat produced from fuel combustion by a specific way of: connecting, a gas outlet of a combustion device to a conveying pipe, and further connecting the conveying pipe to a gas inlet of the reactor or an air chamber aeration nozzle at a lower part of the reactor.

A wind turbine is connected in series between conveying pipes.

The fuel comprises coal, natural gas, diesel oil, heavy oil, or biomass.

The organic waste in the reactor is heated using the waste gas with heat produced from fuel combustion by a specific way of: mixing the waste gas with heat with external air according to a preset ratio, and ventilating the mixture into the reactor of aerobic fermentation to heat the organic waste in the reactor of aerobic fermentation.

The chemical substances in the waste gas with heat absorbed by the organic waste in the reactor comprise $SO_2$, $NO_2$ $CO_2$, and dioxin.

The tee valve and the ratio adjusting device are capable of mixing the waste gas and the external air according to the preset ratio.

The organic waste in the reactor is heated using the waste gas with heat produced from fuel combustion under the control of a controller; an oxygen sensor and a temperature sensor are mounted at a discharge end of the reactor, outputs of the oxygen sensor and the temperature sensor are connected to corresponding inputs of the controller respectively, and the controller is capable of comparing input values from the sensors with present values so as to control a tee valve and a ratio adjusting device for mixing the waste gas with heat with external air according to a preset ratio; when the controller detects that oxygen content from the oxygen sensor is lower than a present lower limit value, the controller controls the tee valve and the ratio adjusting device to increase the ratio of the external air, and when the controller detects that the oxygen content from the oxygen sensor is higher than a preset upper limit value, the controller controls the tee valve and the ratio adjusting device to decrease or zero the ratio of the external air; when the controller detects that temperature from the temperature sensor is higher than a present value, the controller controls the tee valve and the ratio adjusting device to decrease or zero the ratio of the waste gas; and when the controller detects that the temperature from the temperature sensor is lower than a present value, the controller controls the tee valve and the ratio adjusting device to increase the ratio of the waste gas.

The waste gas with heat is mixed with the external air according to the preset ratio before being ventilated into the reactor of aerobic fermentation, and the preset ratio is 0~1:1~0.

Embodiment 1

Waste gas, generated from the combustion of fuels such as coal, natural gas, biomass, and diesel oil and so on, is communicated with an electric tee valve through pipes, and another end of the electric tee valve is communicated with air. The electric tee valve is configured for adjusting the ratio of hot waste gas and cold air that enter into the fermentation reactor. The mixed gases are blown into the fermentation reactor by a wind turbine to heat the materials in the fermentation reactor.

When the actual temperature of the reactor or the materials to be fermented is lower than a present temperature of the reactor, the temperature of the reactor is increased by increasing the ratio of the hot waste gas, decreasing the ration of the air, and/or increasing output power of the boiler. When the actual temperature of the reactor or the materials to be fermented is higher than a present temperature of the reactor, the temperature of the reactor is decreased by decreasing the ratio of the hot waste gas, and/or decreasing output power of the boiler.

Embodiment 2

Waste gas, generated from the combustion of fuels such as coal, natural gas, biomass, and diesel oil and so on, is communicated with an electric tee valve through pipes, and another end of the electric tee valve is communicated with air. The electric tee valve is configured for adjusting the ratio of hot waste gas and cold air that enter into the fermentation reactor. An exhaust fan is mounted at an exhaust end of the fermentation reactor. The mixed gases enter into the fermentation reactor under the negative pressure of the ventilation to heat the materials in the fermentation reactor.

When the actual temperature of the reactor or the materials to be fermented is lower than a present temperature of the reactor, the temperature of the reactor is increased by increasing the ratio of the hot waste gas, decreasing the ration of the air, and/or increasing output power of the boiler. When the actual temperature of the reactor or the materials to be fermented is higher than a present temperature of the reactor, the temperature of the reactor is decreased by decreasing the ratio of the hot waste gas, and/or decreasing output power of the boiler.

The gas drawn from the fermentation reactor is cooled by a cooling device before being sent into and absorbed by a biological filtration tower, and is discharged when achieving the discharge standard. When the fermentation is finished, a waste gas input pipe in the electric tee valve is closed, the ventilation speed is increased to decrease the temperature of the materials sharply, and the materials are discharged.

Embodiment 3

Waste gas, generated from the combustion of fuels such as coal, natural gas, biomass, and diesel oil and so on, is communicated with an electric tee valve through pipes, and another end of the electric tee valve is communicated with air. The electric tee valve is configured for adjusting the ratio of hot waste gas and cold air that enter into the fermentation reactor. Exhaust fans are mounted at both the exhaust and feed ends of the fermentation reactor. The mixed gases enter into the fermentation reactor under the cooperation action of the two exhaust fans to heat the materials in the fermentation reactor. When the actual temperature of the reactor or the materials to be fermented is lower than a present temperature of the reactor, the temperature of the reactor is increased by increasing the ratio of the hot waste gas, decreasing the ration of the air, and/or increasing output power of the boiler. When the actual temperature of the reactor or the materials to be fermented is higher than a present temperature of the reactor, the temperature of the reactor is decreased by decreasing the ratio of the hot waste gas, and/or decreasing output power of the boiler.

The gas drawn from the fermentation reactor is cooled by a cooling device before being sent into and absorbed by a biological filtration tower, and is discharged when achieving the discharge standard. When the fermentation is finished, a waste gas input pipe in the electric tee valve is closed, the ventilation speed is increased to decrease the temperature of the materials sharply, and the materials are discharged.

I claim:

1. A method for facilitating an aerobic fermentation reaction using combustion waste gas, the method comprising:
    providing an aerobic fermentation reaction system which comprises a combustion device, a conveying pipe, an electric tee valve, a wind turbine and a reactor, wherein a gas outlet of the combustion device is connected to a gas inlet of the reactor or an air chamber aeration nozzle at a lower part of the reactor via the conveying pipe; the wind turbine is located at a middle of the conveying pipe; the electric tee valve is located on the conveying pipe and between the wind turbine and the combustion device, so that the electric tee valve is capable of allowing the pass and mix of waste gas produced by fuel combustion in the combustion device and external air to generate a mixed gas into the reactor; wherein the waste gas comprises heat energy;
    introducing, by the wind turbine, the mixed gas to the reactor through the conveying pipe;
    wherein the reactor has organic waste therein;
    adjusting the mixing ratio of the waste gas and the external air to facilitating the fermentation reaction in the reactor, so that part of chemical substances in the waste gas is absorbed by the organic waste;
    performing an environmental friendly treatment on the waste gas, and drawing the gas from the fermentation reactor.

2. The method for facilitating an aerobic fermentation reaction using combustion waste gas according to claim 1, wherein, fuel in the fuel combustion is selected from the group consisting of: coal, natural gas, diesel oil, heavy oil, and biomass.

3. The method for facilitating an aerobic fermentation reaction using combustion waste gas according to claim 1, wherein, the part of the chemical substances in the waste gas absorbed by the organic waste in the reactor is selected from the group consisting of: $SO_2$, $NO_2$, $CO_2$, and dioxin.

4. The method for facilitating an aerobic fermentation reaction using combustion waste gas according to claim 1, wherein the aerobic fermentation reaction system further comprises a controller, an oxygen sensor and a temperature sensor; the oxygen sensor and the temperature are mounted at a discharge end of the rector, and connected, respectively, to the controller; the controller is configured to control the ratio adjustment of the waste gas and the external air through inputs of the oxygen sensor and the temperature, when the controller detects that oxygen content from the oxygen sensor is lower than a present lower limit value, the controller controls the electric tee valve increase the input of the external air;

when the controller detects that oxygen content from the oxygen sensor is higher than a preset upper limit value, the controller controls the electric tee valve to decrease or zero the ratio of the external air;

when the controller detects that temperature from the temperature sensor is higher than a present value, the controller controls the electric tee valve to decrease or zero the ratio of the waste gas; and when the controller detects that temperature from the temperature sensor is lower than a present value, the controller controls the electric tee valve to increase the ratio of the waste gas.

\* \* \* \* \*